United States Patent [19]

McDonald

[11] 3,933,439

[45] Jan. 20, 1976

[54] BLOOD COLLECTION DEVICE

[76] Inventor: Bernard McDonald, 24826 Malibu Road, Malibu, Calif. 90265

[22] Filed: Apr. 29, 1974

[21] Appl. No.: 464,807

[52] U.S. Cl.................. 23/259; 128/2 F; 128/2 G; 73/425.2; 73/425.6; 206/223
[51] Int. Cl.[2]. G01N 1/12; G01N 1/14; G01N 33/16
[58] Field of Search...... 23/259, 292, 253 R, 230 B; 128/2 F, 2 G; 73/425.2, 425.6

[56] References Cited
UNITED STATES PATENTS

| | | | |
|---|---|---|---|
| 3,640,388 | 2/1972 | Ferrari................................ | 128/2 F |
| 3,645,252 | 2/1972 | Gilford............................... | 128/2 F |
| 3,785,367 | 1/1974 | Fortin et al......................... | 128/2 F |

FOREIGN PATENTS OR APPLICATIONS

| | | | |
|---|---|---|---|
| 1,208,412 | 10/1970 | United Kingdom................ | 128/2 F |

*Primary Examiner*—R. E. Serwin
*Attorney, Agent, or Firm*—Christie, Parker & Hale

[57] ABSTRACT

This device is for taking a sample of blood from a patient and dispensing a predetermined volumetric sample for analysis. A blood collection needle is in fluid communication with the interior of a closed longitudinally collapsible container such as a bellows having substantially rigid ends. The bellows is elastically compressed from its normally extended position to decrease the interior volume and it is temporarily secured in the compressed position. Once the needle is in place for drawing blood, the bellows is manually released and its elastic extension assists in withdrawing a sample. Samples from the device are dispensed by recompressing the bellows so that some of the blood overflows through a passage into a "ladle" in the top portion of the container. A measured sample is then withdrawn by removing the cap from an outlet tube from the ladle. A plurality of outlet tubes may be used for samples of different predetermined volumes. If desired, an auxiliary sample can be withdrawn by way of a T adjacent the needle. The T can be used for dispensing a sample without measurement or a controlled volume can be dispensed from another exit aperture in related embodiments.

10 Claims, 10 Drawing Figures

U.S. Patent  Jan. 20, 1976  Sheet 1 of 3  3,933,439
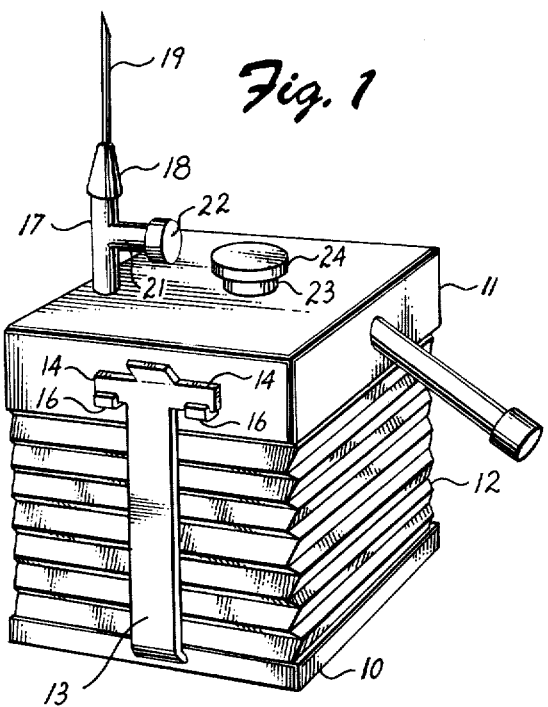
Fig. 1
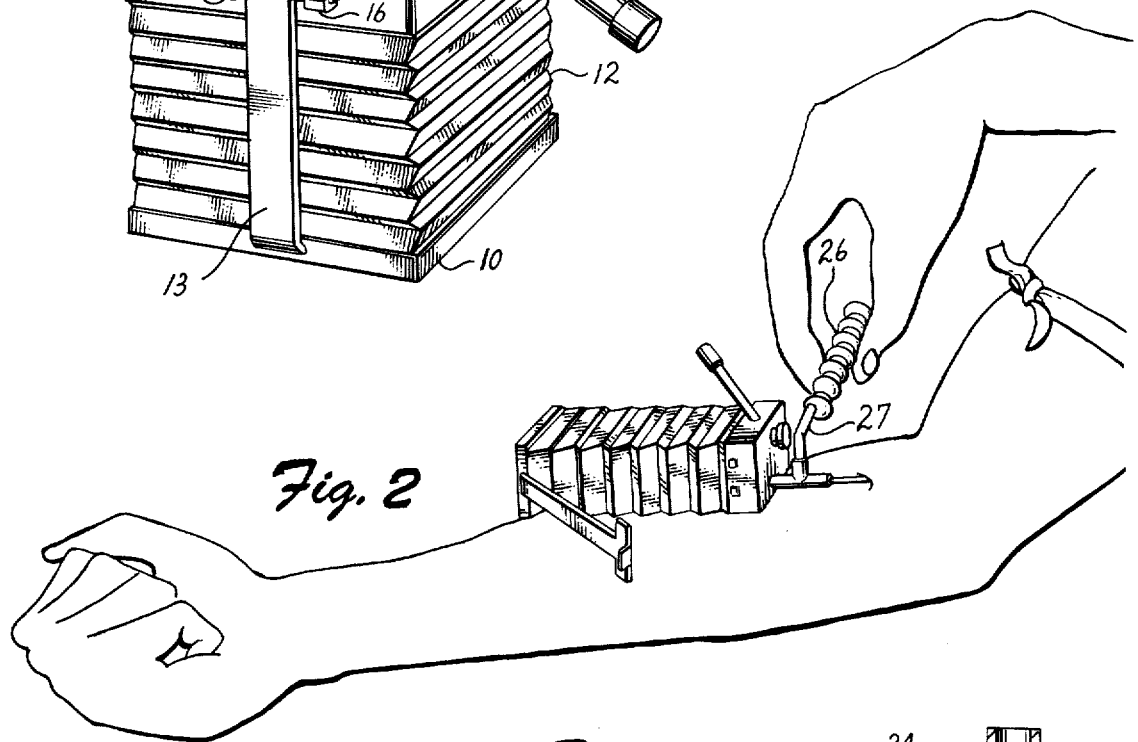
Fig. 2
Fig. 3
Fig. 4
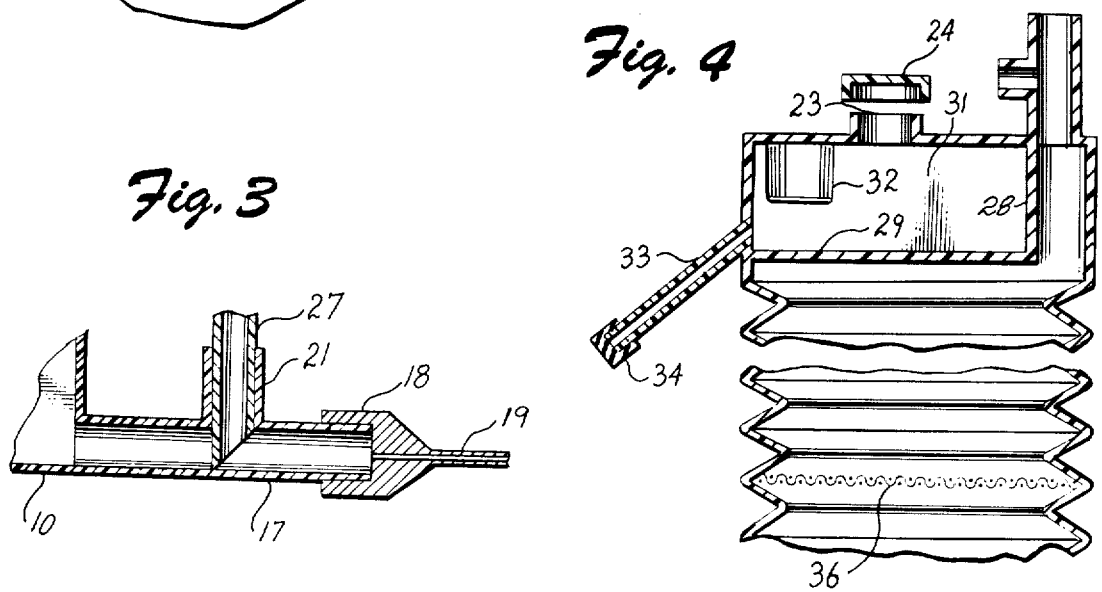

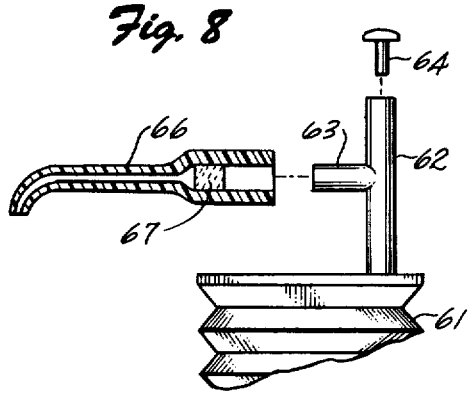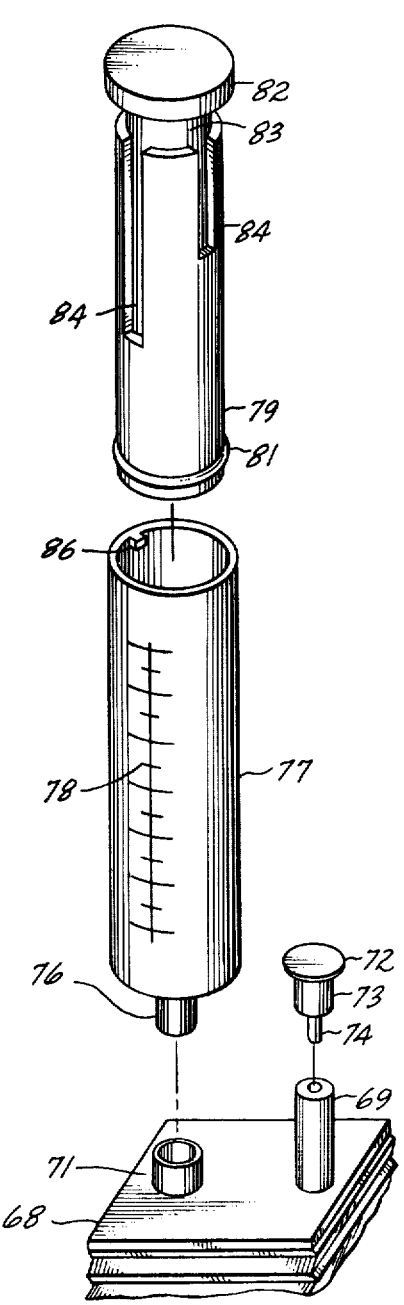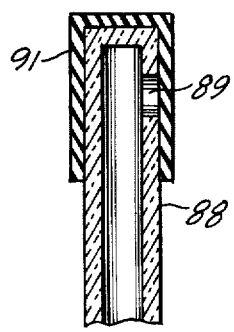

BLOOD COLLECTION DEVICE

BACKGROUND

Very commonly samples are taken of a patient's blood for laboratory tests. This blood is obtained from the patient's veins by means of a hypodermic needle inserted into a suitable superficial vein which has been previously distended by means of a tourniquet. The required quantity of blood is drawn into the syringe by pulling on the barrel of the instrument.

More recently the conventional syringe has been partially replaced by a technique employing a series of preevacuated containers. When such a system is used, a single needle penetrates the vein and a series of evacuated containers are sequentially connected thereto for drawing a number of blood samples for different analyses. The individual containers are advantageous since they are disposable and presterilized and can secure consistent blood volume.

Such an arrangement can have problems, however, since the angle of vein penetration is sometimes awkward when the container is large. In some instances the puncture needle has been placed eccentrically on the container to minimize this problem. When the individual preevacuated containers are changed there is a significant chance that the puncture needle will be displaced or will penetrate the opposite wall of the vein. In either case this necessitates an additional puncture and often results in hematoma formation. The condition of the patient's vein and the skill of the operator are important factors in determining whether this may occur.

In addition, the preevacuated collection tubes often contain a substance such as an anticoagulant or blood preservative which can have significant adverse effects on the patient if it is aspirated into the patient's bloodstream. Such could happen, for example, if the container has developed a leak and the vacuum has been lost. This condition cannot be ascertained by simple inspection and careless work on the part of the person taking the sample could lead to undesirable or toxic substances entering the patient's bloodstream.

Blood is composed of a solid component, namely the red blood cells, platelets, and white cells and a fluid component or plasma. These components can be separated and depending on the tests being carried out it is desirable to select any of three or four fractions of the blood sample. Whole blood is desirable for red blood cell counts, white blood cell counts, platelet counts and erythrocyte sedimentation rates. When whole blood is desired the blood is collected into an anticoagulant substance such as calcium oxalate or heparin. Plasma is sampled for measurement of blood albumin, globulin, fibrinogen, and protein electrophoresis, and is employed in cross matching of blood. Plasma is the liquid portion of the blood obtained after centrifuging anticoagulated blood. Serum is the fluid left after blood has coagulated. It is essentially plasma without its proteins which remain in the coagulated portion. In addition, it may be desirable for some tests to obtain a sample rich in the so-called buffy layer which remains after centrifuging as a thin layer rich in white blood cells atop the heavier red blood cells.

Due to different concentrations of body chemicals inside the blood cells and outside in the plasma or serum it is essential for most tests to separate the cells from the plasma rather quickly after blood has been withdrawn from veins and before the contents of the cells leak out into the plasma.

Ordinarily when blood samples are taken, analysis is made on whole blood or on the serum remaining as a supernatant liquid following blood coagulation, or alternatively on the liquid plasma which overlies precipitated solid elements of the blood. It is desirable to provide a technique for safely and quickly collecting blood from the patient, and separating blood into the desired fractions. Various tests require samples of predetermined volume and it is helpful to the laboratory technician to have simple means for rapidly and reliably taking samples of measured volume.

BRIEF SUMMARY OF THE INVENTION

There is, therefore, provided in practice of this invention according to a presently preferred embodiment a blood collection device in the form of a closed, longitudinally collapsible elastic container that is normally extended to have a larger interior volume and is elastically compressed to a position having a smaller interior volume. A blood collection needle connected to the container permits drawing blood from a patient. Manually releasable means are provided for temporarily securing the container in its compressed position so that when released its inherent elasticity increases the interior volume and assists in drawing blood.

Preferably the container has a ladle within the top portion with an overflow passage between the ladle and the balance of the interior of the container. An outlet tube from a lower portion of the ladle permits withdrawing a sample of measured volume. As an alternate to the ladle means of separating, filtering and dispensing of precise measured volumes are provided by external attachments.

DRAWINGS

These and other features and advantages of the present invention will be appreciated as the same becomes better understood by reference to the following detailed description of a presently preferred embodiment when considered in connection with the accompanying drawings wherein:

FIG. 1 illustrates in perspective a blood collection device constructed according to principles of this invention in its compressed condition;

FIG. 2 illustrates the device in its normally expanded condition for drawing a blood sample, and also an accessory for drawing a second sample;

FIG. 3 is a transverse cross section indicating connection of the accessory to the blood collection device;

FIG. 4 is a vertical cross section through the blood collection device;

FIG. 8 is an exploded, fragmentary side view, partly in cross section of an alternative arrangement for dispensing a sample;

FIG. 9 illustrates in an exploded view another means for dispensing a sample of controlled volume; and FIG. 10 illustrates in fragmentary, longitudinal cross section a pipette for receiving a measured volume sample.

DESCRIPTION

Figure 5:
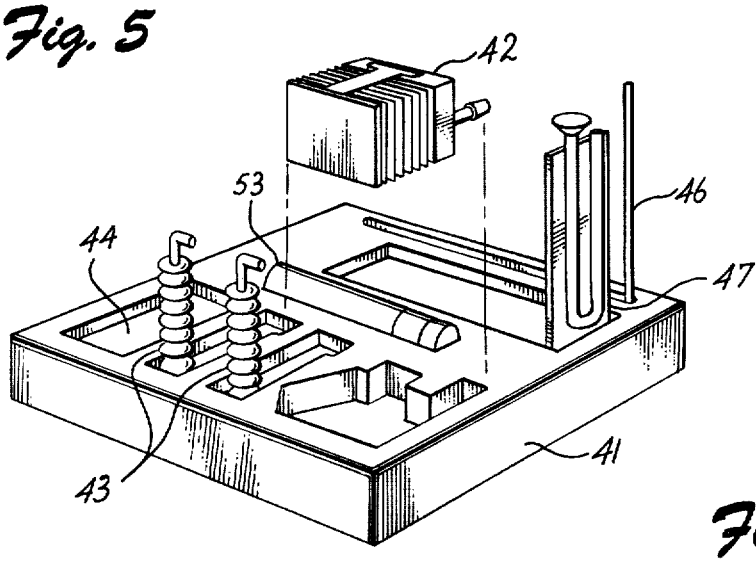
FIG. 5 illustrates in perspective a kit containing the collection device and accessories for blood collection and analysis.

A blood collection device constructed according to principles of this invention is illustrated in perspective in FIG. 1 temporarily latched in a collapsed or compressed position. FIG. 2 is a perspective view of the device as used for drawing blood from a vein in a person's arm. FIG. 4 is a vertical cross section of the blood collection device indicating the interior construction thereof for dispensing a measured volume sample. Since used in the orientation of FIG. 1 for dispensing of blood samples, the positions illustrated in that figure are used herein for convenience in description.

The blood collection device has a substantially rigid flat base 10 so that the device can be placed upright on a table, or the base may be grasped by the person taking the blood sample as hereinafter described. The top portion 11 is also substantially rigid. The top and bottom portions are interconnected by an elastically collapsible envelope in the form of a rectangular corrugated bellows 12. The bellows and top and bottom portions are preferably made of transparent plastic by blow molding or similar techniques. Translucent plastic can be used but is less preferable since it is desirable to view the collected sample with clarity. Inserts or other stiffening arrangements such as ribs can be used for rigidifying the end portions while leaving the bellows flexible. As molded the bellows is normally relatively extended so that the interior volume of the device is relatively large. The plastic is sufficiently elastic that the bellows can be longitudinally compressed into a position wherein the interior volume of the device is relatively small. A pair of plastic straps 13 are connected to opposite sides of the base 10 and have laterally extending ears 14 near their upper end. The ears can be temporarily secured into small hooks 16 on the sides of the top portion 11 of the device. The straps thus serve to temporarily secure the blood collection device with the bellows in its elastically compressed position.

A tube 17 extends upwardly from the top portion 11 for receiving the ferrule 18 of a conventional venapuncture needle 19. The tube 17 is eccentrically located on the top so as to be quite near one side of the device for facilitating taking a blood sample. A side arm 21 on the tube 17 is normally closed by a rubber cap 22.

A vent 23 in the top 11 is also normally closed by a rubber cap 24.

When the blood sampling device is packaged for use the entire assembly is sterilized and packaged in a sterile container or plastic wrapping so as to maintain sterility until use. Ordinarily the tube 17 is sealed by a removable cap and replaced by the sterile needle just prior to use. When packaged the straps 13 are in place as illustrated in FIG. 1 so that the ears 14 engage the hooks 16 and keep the bellows 12 in its compressed condition.

The person taking the blood sample removes the device from its sterile package and installs the needle if necessary. The device is then manipulated so that the needle punctures a patient's vein in the usual manner. The straps 13 are then manually snapped off of the hooks thereby releasing the bellows. The elastic memory of the plastic causes the bellows to expand, thereby increasing the internal volume of the blood sampling device, and the resultant lowered pressure assists in drawing a blood sample. If desired the person taking the sample can also gently pull on the base 10 to assist expansion and assure an adequate blood sample. This is done by grasping the top to hold the needle in place and drawing back on the base, much like the plunger is withdrawn in a conventional syringe. An internal thread or external straps (not shown) can be included to prevent undue elongation of the bellows.

Ordinarily the blood collection device is empty when used and free of reagents that might react with the blood. This permits the blood collected therein to coagulate in the usual manner for separation of the serum plasma fraction from the red cell fraction. In some diagnostic tests samples of whole blood treated with heparin or other anticoagulants are desirable and means are therefore provided for obtaining such samples without again puncturing the patient's vein.

Thus, as illustrated in FIG. 2 after the straps 13 have been released and the bellows expanded to draw at least some blood into the collection device, an additional whole blood sample can be taken from the side arm 21 on the tube 17 leading to the needle. For this purpose a smaller circular bellows shaped container 26 is preferably used. An L-shaped tube 27 extends from one end of the bellows 26 and is eccentrically placed on the end so that when the end of the tube 27 is pointed downwardly, as it is when taking a sample, the juncture of the tube and the bellows is near the top. Chemicals that prevent coagulation can have an adverse effect on a patient if introduced into the blood stream and the chance of inadvertent administration of such material to a patient is avoided by placing the tube inlet high on the container.

To use the auxiliary blood collection device 26 the belllows is manually compressed and the end of the L-shaped tube 27 is put into the side arm 21 of the principal blood collection device. Alternatively the auxiliary device may be packaged in a compressed state and released to elastically expand in the same manner as the principal device. A U-shaped clip overlapping the ends is suitable for holding it in a compressed position. The end of the L-shaped tube is cut on the diagonal as illustrated in FIG. 3 so that the opening faces towards the needle 19 when the auxiliary device is introduced from the right side. The end of the L-shaped tube thus blocks the passage from the tube 17 on the blood collection device and assures that most, if not all, of the blood drawn into the auxiliary device 26 comes directly from the vein rather than being extracted from the principal blood collection device. If one wishes to draw a sample from the principal device, the auxiliary device is inserted from the left side to block the opposite end of the tube 17.

The blood is drawn into the auxiliary device by release of the bellows, which in its normal expansion causes a reduced pressure to aid in drawing the sample. If desired the auxiliary blood collection device can be in the form of a cylindrical tube, collapsible by pinching the sides, however, it is found that greater volumetric efficiency is obtained with a bellows construction.

As illustrated in FIG. 4, a separate compartment 28 is provided in the top portion 11 of the blood collection device for isolating samples of measured volume rather quickly and without pipetting or other tedious extraction techniques. Since this compartment is used in the manner of a ladle for obtaining aliquots of blood or serum it is referred to herein as a ladle. The ladle 28 is most simply formed by a bottom wall 29 separating it from the balance of the interior of the container and a pair of side walls 31 spaced apart from the side walls of the top portion 10. The other two side walls forming a ladle are preferably side walls of the top. An overflow passage or weir 32 is provided through one of the side walls 31 to provide fluid communcation between the ladle and the balance of the container. Preferably the overflow passage is on the side remote from the tube 17 so that the ladle does not fill as the device is initially used for drawing a blood sample. An outlet tube or spout 33 extends from a lower portion of the ladle 28 to the outside of the container. The outlet end of the tube is normally sealed by a rubber cap 34.

When one wishes to withdraw a sample from the blood collection device it is placed upright on a table or other convenient support. The technician presses down on the top portion thereby compressing the bellows 12. The cap 24 on the vent 23 may be opened or air can escape through the tube 17 by which blood was drawn originally. When the top portion is pressed down the overflow passage 32 dips into the blood or serum within the collection device and the ladle fills. When the top is released and the ladle rises, any excess liquid flows back until the liquid level within the ladle is even with the bottom of the passage. The volume of liquid received within the ladle is therefore determined by the volume beneath the level of the overflow passage.

The sample is then removed from the ladle by taking the cap 34 off of the spout 33 and permitting the liquid to flow into a test tube or other suitable sample receptacle. The top can be depressed as many times as desired for dipping the ladle into the liquid in the container for obtaining multiple samples or larger samples. If desired, the top can be pressed down while the cap is off the spout to simply dispense liquid without measurement.

If desired when serum samples are to be collected, a fine pore filter can be provided in the overflow passage 32 to strain out small aggregates of fibrin in the serum. Alternatively, the floor of the ladle can be a filter of fine porosity through which serum can be squeezed by compression of the top with the vent 23 open. When the vent is closed, the filter effectively resists counterflow of liquid so that the ladle remains full until the desired sample is removed.

One feature of plastic containers for blood is that the plastic is nonwettable. This discourages clots from adhering to the walls of the container which is advantageous, but the same quality is a disadvantage in that the clotting is retarded and delays may cause a change in the chemistry of the serum.

A screen 36 or perforated disk is therefore positioned within the bellows and is ordinarily held in place simply by being enfolded within the bellows. This disk is ordinarily of plastic with glass fragments, beads or the like, exposed on the surfaces like sandpaper to provide a site for clotting. The glass surfaces not only accelerate clotting, but also the perforated disk can serve to anchor the resultant clot within the container.

FIG. 5 illustrates in perspective a kit particularly suited for taking and analyzing blood specimens. The kit not only provides a convenient package for the most common items used in analysis, but also serves as a support stand for some of the items. The kit has a tray 41 with a series of receiving pockets. It will be recognized that some of the items contained in the kit may be wrapped or otherwise contained in sterile packages and these may be included although not illustrated. Preferably, the kit is assembled and the entire structure, tray and all, is sterilized and packaged.

In one of the pockets in the tray 41 there is a blood collection device 42 as hereinabove described and illustrated. Two or more auxiliary blood collection devices 43 may also be included in the kit. Such devices are similar to that hereinabove described and illustrated in FIG. 2 and may contain anticoagulants or other common blood analysis reagents. A microscope slide 44 is contained in another pocket in the tray. Preferably, the microscope slide is a self-smearing slide of the type described in my co-pending patent application entited "Urine Collection and Analysis Device" Ser. No. 363,383, filed May 24, 1973.

A conventional microhematocrit tube 46 is provided in the kit and if desired, a small dab or gum may be provided in or near that pocket to "stopper" the microhematocrit tube after it has been filled. This tube is ordinarily filled by capillary action when touched to the side arm 21 (FIG. 1) on the blood collection device after it has been removed from the patient's vein and before standing upright.

Figure 6:
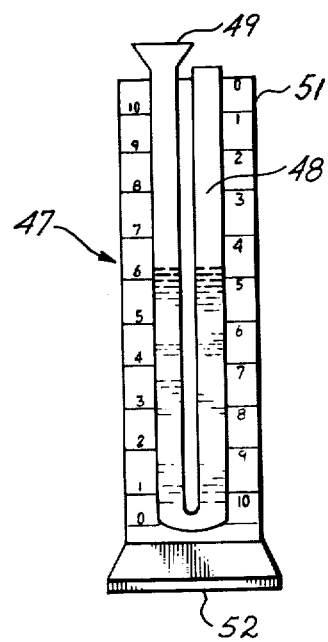
FIG. 6 illustrates in perspective a tube for sedimentation analysis.

A U-shaped sedimentation tube 47, also illustrated in FIG. 6, is preferably included in the kit. One problem with sedimentation rate tests is the care that must be taken in placing the sample in the sedimentation tube. Ordinarily, a Pasteur pipette is used and introduced into the bottom of the sedimentation tube for gradual filling from the bottom to avoid bubbles.

The sedimentation tube provided in the kit has a U-shaped transparent tube 48, one opening of which has a funnel shaped mouth. A blood sample introduced into the funnel shaped mouth runs down one arm of the U-shaped tube and fills the other arm from the bottom. The ease of reliable filling more than offsets the small additional amount of blood required for this type of sedimentation tube. A backing sheet 51 behind the U-tube 48 provides measuring indicia that are clearly readable and a support base 52 keeps the sedimentation tube upright. Alternatively, the backing sheet 51 can be longer at the bottom and fit into a slot in the tray 41 to be held upright.

It will be apparent that other items useful in blood analysis, such as a needle storage tube 53, centrifuge tube or other items may be included in the collection and analysis kit.

Figure 7:
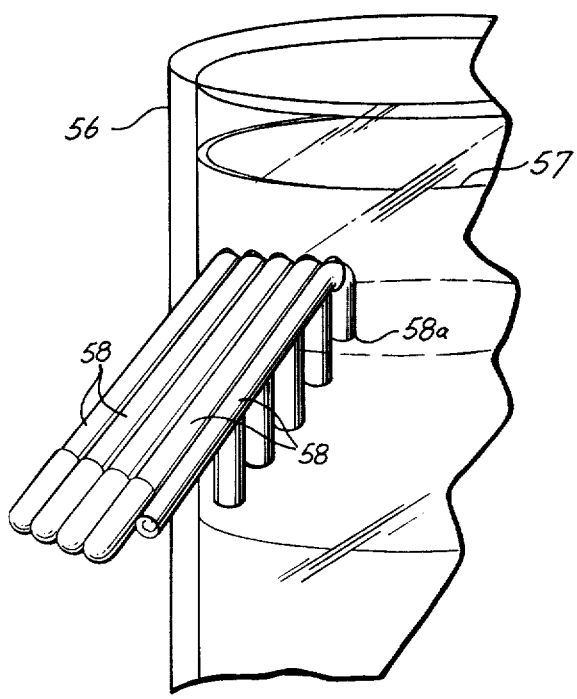
FIG. 7 is a fragmentary view of an alternative arrangement for dispensing measured volumes of blood.

FIG. 7 illustrates in fragmentary perspective a slightly different embodiment of ladle and extraction spout for a blood collection device constructed according to principles of this invention. In this case the collection container 56 is indicated to be circular rather than the rectangular form hereinabove described and illustrated in FIG. 1. The ladle 57 is in the form of a separate basinlike member secured within the top portion of the blood collection device so that it is spaced apart from the top and blood can overflow its edges for filling.

A plurality of outlet tubes or spouts 58 dip into the ladle and extend to the outside of the container. Each of the outlet tubes or spouts 58 is ordinarily sealed by a cap 59. The inside diameter of the outlet tubes is small enough that they can fill by capillary action for starting a siphon. Alternatively, the upper portion of the outlet tubes can be below the upper liquid level in the ladle when filled so as to be self-priming.

When the blood collection device illustrated in FIG. 7 is used, it is filled in the same general manner as hereinabove described and the ladle 57 is filled by depressing the top until the liquid overflows into the ladle. Thereafter the cap 59 on one of the outlet tubes is removed and liquid in the ladle above the inlet to that tube flows out and into an analysis vessel. Thus, for example, if the cap is removed from outlet tube 58a, the liquid will drop only to the level indicated in FIG. 7. The volume of liquid between that point and the top of the ladle being well known provides a sample of known quantity. Since the ends of the several outlet tubes 58 are at different levels within the ladle, various size samples can be withdrawn by removing the cap from any selected tube and draining the quantity of liquid above its entrance to either the entrance of a higher tube or to the top of the ladle.

Instead of using a sample cap that merely fits over the end of the outlet tube or spout, a stopper may be used having a long rod that fits into the tube. This has an advantage in limiting the volume of liquid within the tube so that the measured volume is only that within the ladle and better measurement accuracy is obtained. Further, when such a rod-like stopper is withdrawn from the outlet tube it helps draw liquid into the tube for "priming" it for continued liquid flow.

The means for controlling the volume of sample dispensed from the elastically collapsible container may be external rather than within the container. Thus, for example, in FIG. 8 a simple dispenser from the container is provided without any internal ladle. As illustrated in this embodiment, the elastically collapsible container 61 is in the form of a rectangular bellows. The top portion of the bellows is illustrated herein and the balance is as hereinabove described except that the interior is completely hollow rather than having an internal ladle as in the embodiment of FIGS. 1 through 4. A screen or other means for assuring controlled coagulation may be included.

A tube 62 rises above the top of the container for receiving a needle (not shown) for drawing a blood sample. A side arm 63 on the tube permits drawing on auxiliary sample as hereinabove described. The side arm is ordinarily plugged by a small rubber stopper 64 when a sample is being taken in the main body of the container. After such a sample has been collected, the stopper 64 is removed and put in the upstanding tube 62 for plugging it.

To dispense a sample, the plug is put into the upstanding tube and a dispensing tip 66 is fitted on the side arm 63. A small filter 67 is preferably provided in the dispensing tip to catch any protein particles and to permit dispensing of a filtered sample of liquid. One dispenses a sample simply by pushing down on top of the collapsible container or the tube 62 to squeeze out a sample which flows into any convenient measuring device. It will be apparent that if desired the dispensing tip can be provided with a measured volume dispensing device itself, such as a plunger in a reservoir or ladle as hereinabove described.

FIG. 9 illustrates in exploded perspective a syringe-type sampling device connectable to a collapsible blood sampling container. As illustrated in this embodiment, the sampling container is in the form of a rectangular bellows 68, only the top portion of which is illustrated. A sampling tube 59 on the top receives a needle (not shown) for drawing a blood sample all as hereinabove described. Another tube 71 on the top of the collapsible container is in liquid communication with the inside, preferably by way of a fine filter an appreciable distance below the top to assure withdrawal of a clear liquid sample. A rubber plug 72 has a relatively larger diameter 73 near its cap to fit snugly into the tube 71 and keep it closed during withdrawal of a blood sample from a patient. Thereafter the cap 72 is removed and a smaller diameter portion 74 inserted in the sampling tube 69 to plug it during dispensing of a sample.

Samples of controlled volume are obtained from the collapsible container by a syringe, the tip 76 of which fits into the tube 71 on the top of the collapsible container. The syringe has a barrel 77 with suitable calibration markings 78 indicating the internal volume. A plunger 70 fits into the barrel and is preferably sealed thereto by an O-ring 81. The general nature of such syringes is well known, and other sealing arrangements may of course be used.

Beneath the enlarged top 82 of the plunger, there is a reduced diameter groove 83 extending circumferentially around the plunger. A plurality of longitudinally extending grooves 84 extend from the peripheral groove a predetermined distance along the length of the plunger. One such groove (hidden on the reverse side) extends most of the length of the plunger. A small tab 86 extends inwardly at the upper end of the barrel 77 and fits into the grooves in the plunger (the tab 86 is formed or added after the plunger is assembled in the barrel).

To use the syringe it is inserted in the tube 71 on the top of the collapsible container and the plunger is rotated in the barrel until a selected one of the longitudinal slots 84 in the plunger is aligned with the tab 86 in the barrel. When the collapsible container is squeezed, a sample flows up into the syringe and displaces the plunger. The distance it can move is limited by the tab engaging the end of the respective longitudinal slot 84. The several slots in the plunger each have a predetermined length so that the displacement provides a volume of predetermined size in the syringe. The full length slot permits a full stroke of the plunger so that it can be used with the calibration markings in the usual manner.

FIG. 10 illustrates the top end of a pipette suitable for extracting a sample from a collapsible container as hereinabove described. Such a calibrated pipette can be used in lieu of the syringe described and illustrated in FIG. 9. Such a pipette is in the form of a transparent tube 88, the upper end of which is illustrated in FIG. 10. The lower end of this tube may be inserted in the opening 71 in the top of the collapsible container (FIG. 9) and the pipette filled by collapsing the container in the same general manner as the described syringe is filled.

To fill the pipette the air originally in it must be displaced. A hole 89 is therefore formed in one wall of the pipette near the top and a thin rubber sleeve 91 is positioned over the end so as to block the hole. As a sample is squeezed into the pipette, air can escape from under this sleeve. The sleeve acts as a check valve so that the sample so received does not run from the pipette when it is removed from the collection container. The sample can be dispensed when desired by simply peeling back part of the rubber sleeve.

Although limited embodiments of blood collection device have been described and illustrated herein many modifications and variations will be apparent to one skilled in the art. Thus, for example in order to enhance the elasticity of the plastic bellows, one can imbed or mount a spring within the container. Similarly, instead of a rectangular blood sampling device it can have a circular cross section for the end portions and bellows. The rectangular cross section is preferred so that the collection device will rest stably on a patient's arm as auxiliary samples are taken by way of the T-shaped entrance tube.

The bellows described in the preferred embodiment is advantageous since the internal volume of the blood collection device can be relatively well known, for example, about 20 ml. Alternatively, generally helically extending folds can be provided in the envelope extending between the top and bottom of the device and these parts can twist somewhat relative to each other as the device is longitudinally compressed. The straight bellows is preferred, however, since this twisting can interfere with sampling dispensing.

A check valve can be provided in the inlet tube of the auxiliary collection devices containing anticoagulant so that blood can enter the collection device but the anticoagulant cannot flow in the reverse direction to enter a patient's bloodstream. If this is done, an auxiliary opening for draining blood from the collection device may be needed or the check valve portion can simply be snipped off after a sample is taken.

Many other modifications and variations will be apparent to one skilled in the art, and it is therefore to be understood that within the scope of the appended claims, the invention may be practiced otherwise than as specifically described.

What is claimed is:

1. A blood collection device comprising:
   a closed, longitudinally collapsible elastic container movable between a normally extended position having a larger interior volume and a compressed position having a smaller interior volume;
   a blood collection needle in fluid communication with the interior of the container;
   manually releasable means for temporarily securing the container in its compressed position; and
   a permeable member mounted within the container and including blood clotting sites exposed on the surfaces thereof.

2. A blood collection device comprising:
   a closed longitudinally collapsible elastic container movable between a normally extended position having a larger interior volume and a compressed position having a smaller interior volume;
   a blood collection needle in fluid communication with the interior of the container;
   manually releasable means for temporarily securing the container in its compressed position;
   a ladle having a predetermined volume in the upper portion of the container for receiving an aliquot of blood from the balance of the container;
   an overflow passage between the ladle and the balance of the interior of the container, the overflow passage being above the normal liquid level of a sample of blood in the container; and
   an outlet spout from a lower portion of the ladle to the outside of the container for discharging an aliquot of blood therefrom.

3. A blood collection device as defined in claim 2 comprising a plurality of outlet spouts, the height between the entrance to each outlet spout and the overflow passage defining a different predetermined volume within the ladle.

4. A blood collection device comprising:
   a closed, longitudinally collapsible elastic container movable between a normally extended position having a larger interior volume and a compressed position having a smaller interior volume;
   a blood collection needle in fluid communication with the interior of the container;
   manually releasable means for temporarily securing the container in its compressed position;
   a ladle in an upper portion of the container for collecting an aliquot of blood from the interior of the container;
   a permeable filter between the ladle and the balance of the container for passage of blood therebetween; and
   an outlet spout from a relatively lower portion of the ladle to the outside of the container for discharging an aliquot of blood therefrom.

5. A blood collection device comprising:
   a closed container having a substantially rigid top portion and a collapsible lower portion;
   means connected to the top portion for receiving blood from a patient;
   a ladle fixed within the top portion for receiving an aliquot of blood from the balance of the container upon collapse thereof;
   an overflow passage between the ladle and the balance of the interior of the container for flow of blood therebetween; and
   an outlet spout from a relatively lower portion of the ladle to the outside of the container for discharge of an aliquot of blood therefrom.

6. A blood collection device as defined in claim 5 comprising a plurality of outlet spouts, the height between the entrance to each outlet spout and the overflow passage defining a different predetermined volume within the ladle.

7. A blood collection device as defined in claim 5 further comprising;
   a permeable filter between the ladle and the balance of the container for passage of blood therethrough.

8. A blood collection device as defined in claim 5 wherein the collapsible lower portion has a normally extended position having a larger interior volume and an elastically compressed position having a smaller interior volume.

9. A blood collection device as defined in claim 5 wherein the collapsible portion comprises a corrugated bellows having a normally extended rest position with its two ends spaced relatively further apart, and elastically collapsible to a compressed position with its two ends spaced relatively closer together.

10. A sample collection syringe comprising:
    a hollow barrel;
    means at one end of the barrel for receiving a sample;
    a plunger fittable into the barrel;
    a stop in the barrel for limiting retraction of the plunger; and
    a plurality of stops radially positioned around the plunger for engaging the stop in the barrel, each of said stops limiting retraction of the plunger to a predetermined distance less than the full stroke thereof.

* * * * *

UNITED STATES PATENT AND TRADEMARK OFFICE
CERTIFICATE OF CORRECTION

PATENT NO. : 3,933,439
DATED : January 20, 1976
INVENTOR(S) : Bernard McDonald

It is certified that error appears in the above-identified patent and that said Letters Patent are hereby corrected as shown below:

Column 6, Line 16, "or" should be --of--.

Column 7, Line 38, "on" (second occurrence) should be --an--;

Column 7, Line 62, "59" should be -- 69 --;

Column 7, Line 65, "liquid" should be --fluid--.

Column 8, Line 12, "70" should be --79--.

Signed and Sealed this thirteenth Day of April 1976

[SEAL]

Attest:

RUTH C. MASON
Attesting Officer

C. MARSHALL DANN
Commissioner of Patents and Trademarks